US009550105B2

(12) United States Patent
Lacroix et al.

(10) Patent No.: US 9,550,105 B2
(45) Date of Patent: Jan. 24, 2017

(54) PACING SYSTEM WITH FEEDBACK BASED ADJUSTMENTS

(71) Applicant: Immersion Corporation, San Jose, CA (US)

(72) Inventors: Robert Lacroix, San Jose, CA (US); Danny Grant, Laval (CA)

(73) Assignee: Immersion Corporation, San Jose, CA (US)

( * ) Notice: Subject to any disclaimer, the term of this patent is extended or adjusted under 35 U.S.C. 154(b) by 223 days.

(21) Appl. No.: 13/788,479

(22) Filed: Mar. 7, 2013

(65) Prior Publication Data

US 2014/0257536 A1   Sep. 11, 2014

(51) Int. Cl.
| | |
|---|---|
| *A63B 22/00* | (2006.01) |
| *A63B 71/06* | (2006.01) |
| *G04G 21/02* | (2010.01) |
| *G06F 19/00* | (2011.01) |
| *A61B 5/00* | (2006.01) |
| *A61B 5/11* | (2006.01) |
| *G07C 1/22* | (2006.01) |

(52) U.S. Cl.
CPC .......... *A63B 71/0686* (2013.01); *A61B 5/1118* (2013.01); *A61B 5/486* (2013.01); *A61B 5/7455* (2013.01); *G04G 21/025* (2013.01); *G06F 19/3481* (2013.01); *G07C 1/22* (2013.01)

(58) Field of Classification Search
CPC ............ A63B 2024/0065; A63B 22/00; A63B 24/0003; G10H 1/0008; G10H 1/40; G10H 2210/391

USPC .......................... 482/3; 700/91; 600/301, 595
See application file for complete search history.

(56) References Cited

U.S. PATENT DOCUMENTS

| | | | |
|---|---|---|---|
| 5,921,890 A | 7/1999 | Miley | |
| 8,123,660 B2 | 2/2012 | Kruse et al. | |
| 8,460,219 B2 * | 6/2013 | Miyake .................. | A61B 5/112 600/595 |
| 2008/0310579 A1 * | 12/2008 | Boezaart ................ | A63B 24/00 377/24.2 |
| 2010/0075806 A1 | 3/2010 | Montgomery | |
| 2010/0152545 A1 | 6/2010 | Ramsay et al. | |
| 2010/0152620 A1 | 6/2010 | Ramsay et al. | |
| 2010/0186578 A1 * | 7/2010 | Bowen ..................... | G10H 1/40 84/612 |
| 2011/0166488 A1 | 7/2011 | Miyake | |
| 2012/0212340 A1 | 8/2012 | Kruse et al. | |

FOREIGN PATENT DOCUMENTS

WO          2013028581 A1     2/2013

* cited by examiner

*Primary Examiner* — Kang Hu
*Assistant Examiner* — Jeffrey Wong
(74) *Attorney, Agent, or Firm* — Miles & Stockbridge P.C.

(57) ABSTRACT

A pacing system for pacing an activity receives a desired pace that includes a timing interval and generates a first pace signal based on the desired pace and corresponding to the timing interval. The system receives feedback on an actual pace of the activity and determines if the actual pace is different than the desired pace. When the actual pace is different, the system generates a second pace signal having a timing that is different than the timing interval. When the actual pace is not different, the system generates the second pace signal in accordance with the timing interval.

29 Claims, 3 Drawing Sheets

PACING SYSTEM WITH FEEDBACK BASED ADJUSTMENTS

FIELD

One embodiment is directed generally to a system for pacing, and in particular to a system for pacing that includes feedback adjustments.

BACKGROUND INFORMATION

It is well known that good pacing is critical to athletic performance. A key objective in most endurance sports is to ensure that energy output is spread as best as possible during a race and is maximal at the end so that an athlete can finish as fast as possible. An ideal pace strategy involves the perceptive process of proportioning energy use such that the athlete is never working at too high a level, so as to tire quickly, or at too low a level so as to not reach potential.

It is often difficult for an endurance athlete to judge accurately the pace at which he or she should work to spend the available energy in such a way that the body's resources are almost exhausted when he or she crosses the finish line. To aid in pacing, pacing systems or devices such as a "metronome" are used to transmit a pace to the athlete. A metronome is a periodic signal that provides absolute timing. For example, 60 beats per second ("bps") is typically transmitted to someone as a once per second signal (a short audio beep or click, for example). Regardless of the actual pace of the activity, the pace signal, if it is provided to a user, is unwavering and constant.

However, when trying to perform any number of physical activities at a given pace with the help of a metronome, including for example practicing a short piano composition, it can be difficult to keep right on pace. Since the metronome is not listening or paying attention to the activity in any way, it is completely up to user to integrate the pace suggestion and "play along".

This works well when the user is proficient and the pace of activity is well within their ability. Typically, though, the metronome is a training device that is meant to help a user move beyond their current level of ability. Therefore, the user is typically performing at the very edge of their ability, which can lead to the pace of the activity naturally faltering.

SUMMARY

One embodiment is a pacing system for pacing an activity. The system receives a desired pace that includes a timing interval and generates a first pace signal based on the desired pace and corresponding to the timing interval. The system receives feedback on an actual pace of the activity and determines if the actual pace is different than the desired pace. When the actual pace is different, the system generates a second pace signal having a timing that is different than the timing interval. When the actual pace is not different, the system generates the second pace signal in accordance with the timing interval.

DETAILED DESCRIPTION

One embodiment is a pacing system that provides a pacing indicator as a metronome type pace signal in the form of an audio signal, a haptic effect, a video signal, or other type of indicator. The system includes a feedback loop that determines the actual performance pace and in response adjusts the pace signal accordingly. Therefore, the user is never severely out-of-phase with the current performance.

As described above in connection with a metronome, once a paced user's pace has faltered, even momentarily, the activity is no longer in synchrony with the metronome—the performance is typically out of phase with the metronome signal. If the correct pace is recovered, there is now a constant syncopation between the metronome signal and the activity. This typically is a cause of severe cognitive dissonance, and the user either has the instinct to speed the pace of their performance, trying to "catch up" to the metronome, or the performer will pause and then try to re-engage in the activity at the metronome pace, in synchrony with the signal. Often, the syncopation and cognitive load is so high while trying to "find the beat" in re-gaining synchrony with the metronome, that the user's actual pace oscillates or deviates wildly for a prolonged period of time, until the user senses a definite approach to synchrony and can "re-attach" their performance pace to that of the metronome signal.

Figure 1:
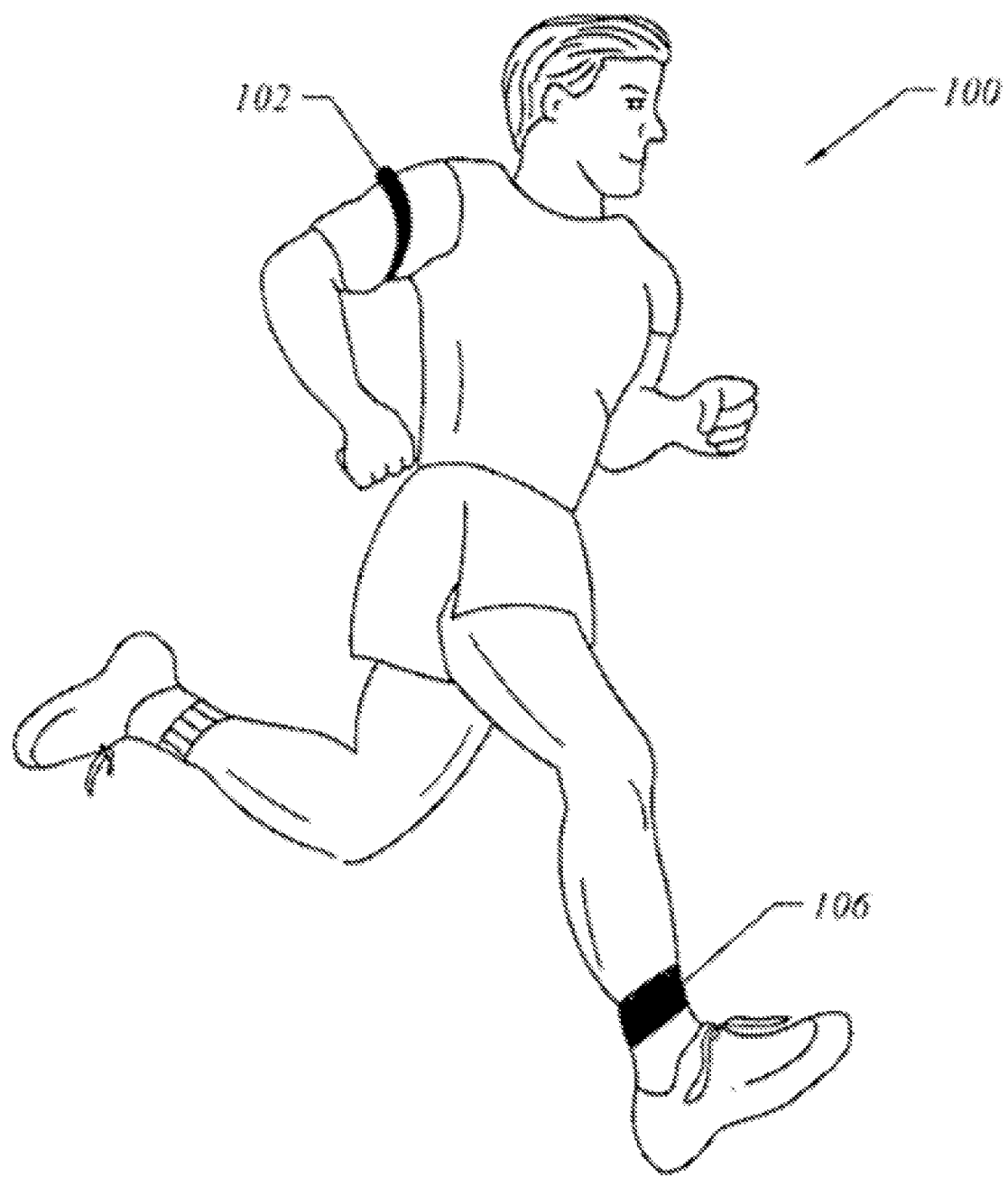
FIG. 1 is a perspective view of a runner wearing a pacing system in accordance with one embodiment of the invention.

FIG. 1 is a perspective view of a runner 100 wearing a pacing system in accordance with one embodiment of the invention. The system shown in FIG. 1 is a haptic pacing system in that it is haptically based. The haptic pacing system/device 102 is configured to attach to the runner's arm and generate a sequence of haptic cues to pace with the runner's strides. System 102 may include multiple sensors for detecting events. Haptic pacing system 102 includes a separate sensing unit 106, which attaches to runner's ankle and senses and collects various runner physical conditions, such as the runner's heart rate, speed, and blood pressure, as well as the current pace of the runner. Some or all of the functionality of sensing unit 106 can be incorporated into system 102 so that a separate unit may not be needed. Further, sensing unit 106 may be located anywhere on runner 100. Haptic pacing system 102, in one embodiment, can be calibrated and/or configured to accommodate the runner's characteristics and/or physical capabilities for optimizing the runner's performance.

Collectively, system 102 and sensing unit 106 includes a sensor and an actuator in one embodiment in which haptic effects are used to provide pacing. Sensors are used to detect conditions of the runner while actuators are used to provide haptic cues such as vibratory effects in accordance with the conditions. For example, a heart rate sensor is capable of sensing a runner's heart rate while a temperature sensor measures the runner's body temperature. Detected information such as heart rate and body temperature are subsequently processed, and a series of haptic cues are generated indicating the optimal runner's pace under the currently detected information.

Sensing unit 106 with multiple sensors is attached to the runner, and unit 106 is coupled to system 102 via a wireless communications network. Unit 106 may be used to detect the runner's heart rate, body temperature, ambient conditions, other runner's physical conditions. It should be noted that system 102 may be configured to manage multiple separate sensing units 106 that can be separately attached to the runner. A function of haptic system 102 is to provide optimal pacing mechanism to improve a runner's performance under the runner's physical as well as ambient conditions. The ambient conditions include uphill, downhill, weather conditions, etc. The feedback mechanism could be located anywhere on the body, such as in the shoe(s), on the wrist, in a helmet, etc. For example, for sensing a heart rate, unit 106 may be in the form of a chest strap, as is known in the art.

In the embodiment shown in FIG. 1, sensing unit 106 functions as a feedback sensor or a pace sensor and can be attached to the ankle as shown or can be attached to a runner's shoe. Haptic system 102 provides the pacing calculation and haptic output and can be worn on the runner's wrist. In another embodiment, a single device can be for example strapped to the wrist and contain both a haptic output device and an accelerometer as the feedback source. In another embodiment, separate measurement and haptic output devices can be used, where the haptic output device is worn in the small of the back, and the feedback and pacing calculation device is contained in a software application running on a mobile computing device that includes an accelerometer.

Figure 2:
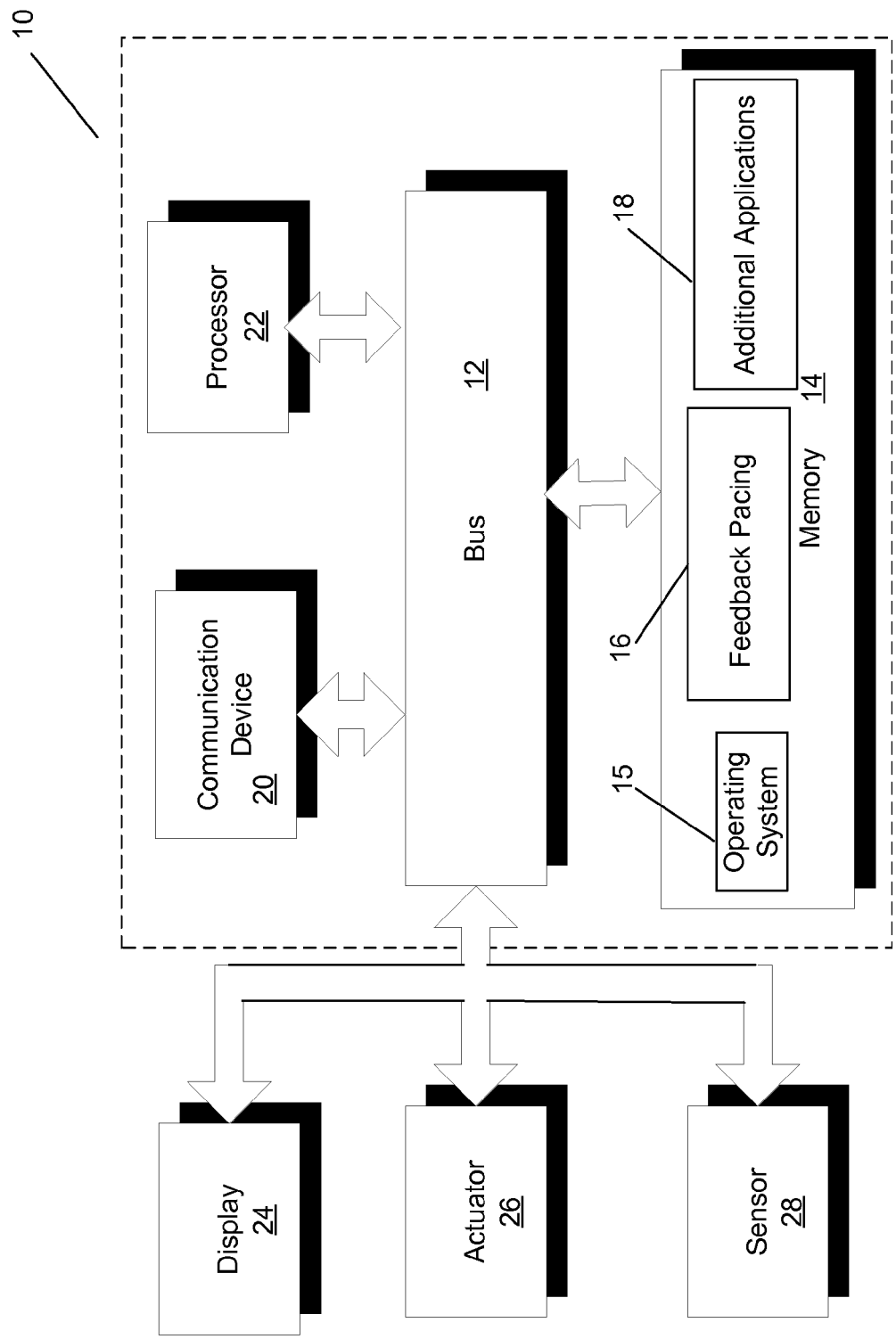
FIG. 2 is a block diagram of a system that can implement the pacing system of FIG. 1 in accordance with one embodiment of the invention.

FIG. 2 is a block diagram of a system 10 that can implement pacing system 102 of FIG. 1 in accordance with one embodiment of the invention. A separate embodiment of system 10 can implement any of the other elements shown in FIG. 1 (i.e., one or more of sensing unit 106). For any of these implementations, all of the elements shown in FIG. 2 may not be needed or present. For example, in an embodiment where haptic effects are not needed for pacing signals, the actuator shown in FIG. 2 may not be included.

System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, flash memory, or any other type of computer-readable medium.

A computer readable medium may be any available medium that can be accessed by processor 22 and may include both a volatile and nonvolatile medium, a removable and non-removable medium, a communication medium, and a storage medium. A communication medium may include computer readable instructions, data structures, program modules or other data in a modulated data signal such as a carrier wave or other transport mechanism, and may include any other form of an information delivery medium known in the art. A storage medium may include RAM, flash memory, ROM, erasable programmable read-only memory ("EPROM"), electrically erasable programmable read-only memory ("EEPROM"), registers, hard disk, a removable disk, a compact disk read-only memory ("CD-ROM"), or any other form of a storage medium known in the art.

In one embodiment, memory 14 stores software modules that provide functionality when executed by processor 22. The modules include an operating system 15 that provides operating system functionality for system 10. The modules further include a feedback pacing module 16 that provides pacing with feedback, as disclosed in more detail below. System 10 will typically include one or more additional application modules 18 to include additional functionality, such as other run training related applications, athletic performance analysis applications, mapping applications, etc.

System 10, in embodiments that transmit and/or receive data from remote sources, further includes a communication device 20, such as a network interface card, to provide mobile wireless network communication, such as infrared, radio, Wi-Fi, or cellular network communication, including communication to and from remote sensor 106 if needed.

Processor 22 is further coupled via bus 12 to a display 24, such as a Liquid Crystal Display ("LCD"), for displaying a graphical representation or user interface to a user. The display 24 may be a touch-sensitive input device, such as a touch screen, configured to send and receive signals from processor 22, and may be a multi-touch touch screen.

System 10 further includes one or more actuators 26 in the haptically enabled embodiments. Processor 22 may transmit a haptic signal associated with a haptic effect to actuator 26, which in turn outputs haptic effects. Actuator 26 may be, for example, an electric motor, an electro-magnetic actuator, a voice coil, a linear resonant actuator, a piezoelectric actuator, a shape memory alloy, an electro-active polymer, a solenoid, an eccentric rotating mass motor ("ERM") or a linear resonant actuator ("LRA").

In addition to actuator 26, system 10 may include other types of haptic output devices (not shown) that may be non-mechanical or non-vibratory devices such as devices that use electrostatic friction ("ESF"), ultrasonic surface friction ("USF"), devices that induce acoustic radiation pressure with an ultrasonic haptic transducer, devices that use a haptic substrate and a flexible or deformable surface or shape changing devices and that may be attached to a user's body, devices that provide projected haptic output such as a puff of air using an air jet, etc. Multiple haptic output devices with multiple haptic effects can generate a pacing signal. Further, the pacing output device can be separate device from system 10 that is in communication with system 10 and is attached to the user such as with a strap or tape or as a wearable device, or integrated into the fabric of clothing or shoes that the user is wearing.

System 10 further includes one or more sensors 28, which may be instead of or in addition to sensor 106 of FIG. 1. Sensors 28 may include an accelerometer, a gyroscope, a Global Positioning System ("GPS") sensor, a touch-sensitive input device (e.g., touch screen, touchpad), a texture stylus, an imaging sensor, or some other type of sensor. Sensors 28 may be configured to detect changes in acceleration, inclination, inertia, or location. Sensors 28 may also include a location sensor, rotary velocity sensor, light sensor, pressure sensor, texture sensor, camera, microphone, or other type of sensor.

As described above in conjunction with FIGS. 1 and 2, in one embodiment system 10 is a device worn by a runner or other type of user that provides a haptic effect to indicate footfall or foot striking pace. For explanation purposes, assume that 60 footfalls per minute is the desired pace, or one footstep per second. With a known pace transmitter such as a metronome, the haptic signal would be provided at every second (i.e., the timing interval). At t=0, t=1 s, t=2 s, a haptic effect or other type of indicator would be felt by the runner, regardless of his/her current performance.

In contrast, pace system 10 in one embodiment provides the runner with the first pace signal at time=0 s. System 10 then monitors a feedback signal coming from one or more sensors. In one embodiment, the feedback signal is generated by an accelerometer that can detect the stomp of the runner's footfall or foot strike. System 10 waits up to t=1 s while implementing the following functionality:

- If the foot fall is detected at t=750 ms (meaning, the pace is 25% faster than the target pace), system 10 resets its pace setting at t=750 ms, plays the pace signal at t=1 s, and sets the next pace signal target to 750 ms+1 s=1.75 s. The runner will feel the haptic effect soon after footfall, telling them their pace is too fast. This resets the tempo relative to the last detected footfall.
- If the footfall occurs within +/−5% of the target pace, meaning within t=950 ms to t=1050 ms, system 10 plays the pace signal at t=1 s, and sets the next pace signal target at t=2 s.
- If the footfall occurs at t>1050 ms, system 10 plays the pace signal at t=1 s, telling the runner that the expected footfall has come too late. System 10 waits for the footfall to occur, for example at t=1250 ms. System 10 sets the next pace signal target to 1250 ms+1 s=2.25 s. This resets the tempo relative to the last detected footfall.

By setting the next pace signal relative to the last detected footfall, there is never the unsettling or confusing pace signal syncopation that confuses the runner for several seconds. Instead, it encourages the runner to speed up or slow down based on their current pace, and the pace system will therefore be more intuitive and pleasant to use.

The generated pace signal could be formed from a wide range of effects and technologies, including audio and video effects, vibrations, deformation, squeezing, poking, stretching, surface friction, heat, etc. The pace signal could also be produced by the system 10 itself or by wearable accessories (e.g., a bracelet, a pair of glasses, shoes, a belt, etc.) or by other remote accessories (e.g., car keys, laptop computers, music players, or any other haptically enabled devices).

Figure 3:
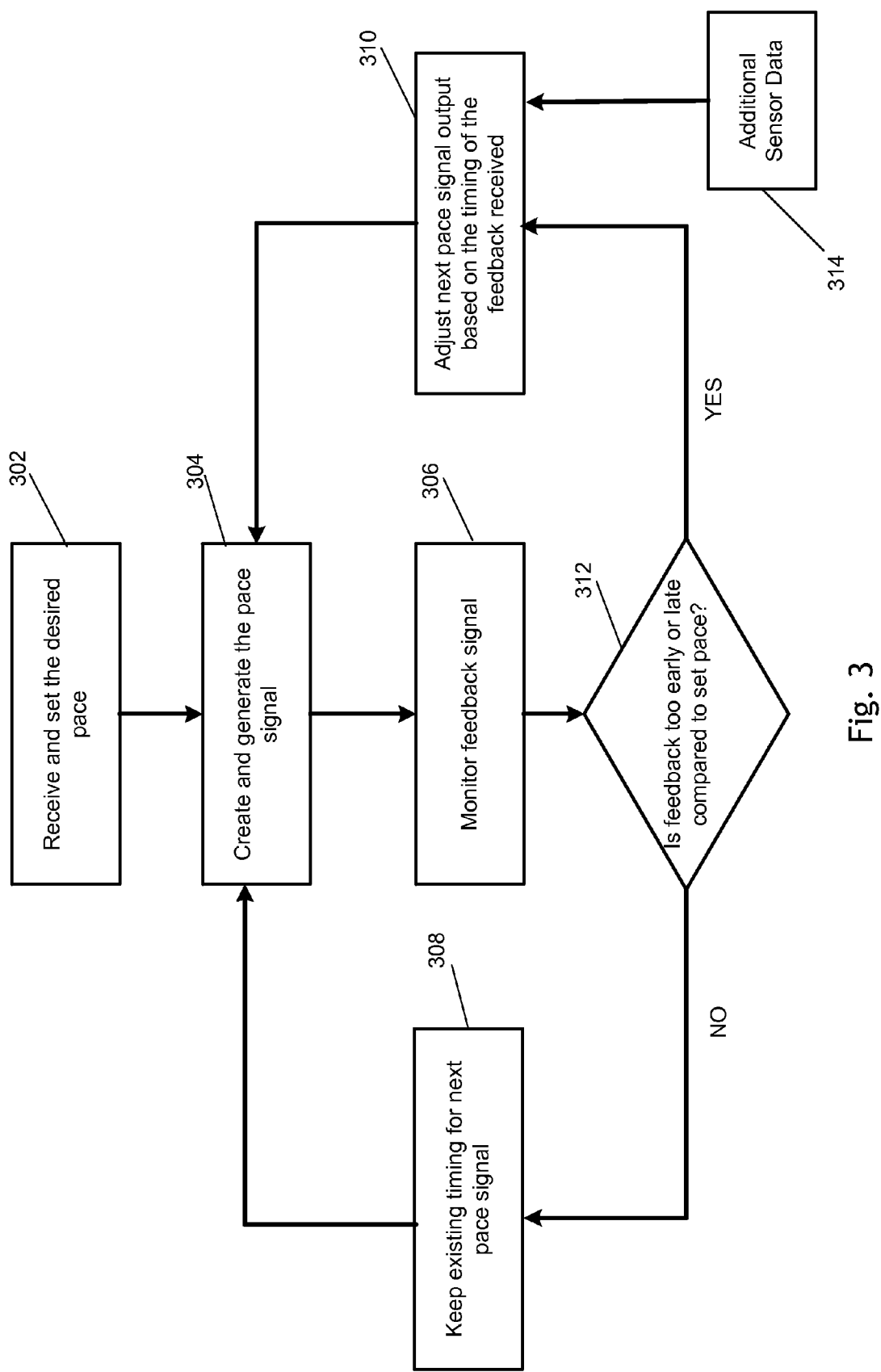
FIG. 3 is a flow diagram of the functionality of a feedback pacing module that provides pacing with feedback in accordance with one embodiment of the present invention.

FIG. 3 is a flow diagram of the functionality of feedback pacing module 16 that provides pacing with feedback in accordance with one embodiment of the present invention. In one embodiment, the functionality of the flow diagram of FIG. 3 is implemented by software stored in memory or other computer readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software.

At 302, the desired pace is received and set. The user sets the desired pace for their activity, using any type of user interface controls on system 10. The activity can be any activity that has a measurable pace.

At 304, the pace signal output is created and generated to communicate the current pace signal to the user. As discussed, the pace signal output could be a tactile (e.g., a vibratory haptics effect), audio, or visual cue, or a combination of these outputs.

At 306, system 10 monitors the feedback signal, looking for the feedback cue. In one embodiment, the feedback is a footfall causing a spike in an accelerometer signal.

At 312, it is determined if the feedback is too early or late compared to the set pace by determining how close to the desired pace the feedback occurred. A determination is made if the feedback occurred within acceptable temporal limits.

If no at 312 (i.e., the feedback signal occurs within the acceptable temporal limits) the existing timing is kept for the next pace signal. System 10 determines the next pace signal output time according to the nominal pace set by the user.

If yes at 312 (i.e., the feedback signal does not occur within acceptable temporal limits), at 310 the next pace signal output time is determined/adjusted based on the timing of the feedback received.

At 310, in addition to the current pace/footfall feedback data, sensor data from multiple sources (received at 314) as discussed above could also be used to modify the pace. For example, if the user wanted their cardiovascular system to operate within a certain heartbeat rate, system 10 could use heart rate monitor data, in addition to footfall data, to adjust the pace based on heart rate and footfall. Further, system 10 can also provide a haptic alert to the user if a limit is exceeded, such as minimum or maximum heart rate.

In one embodiment, when the pace signal at 304 is generated in the form of a haptic effect, different haptic effects can vary and be distinctive to let the user know that the pace is early, on time, or late. A haptic effect can be varied and thus distinctive from other haptic effects (i.e., different haptic effect types) in one embodiment by varying one or more parameters. In general, high level parameters that define a particular haptic effect include magnitude, frequency and duration. Low level parameters such as streaming motor commands could also be used to determine a particular haptic effect. Some variation of these parameters can change the feel of the haptic effect, and can further cause the haptic effect to be considered "dynamic". A first type of haptic effect can indicate an early pace, a second type of haptic effect can indicate an on time pace, and a third type of haptic effect can indicate a late pace. Further, different types of haptic effects can be used to indicate different information, such as exceeding a maximum heart rate, excessive body temperature, etc.

In one embodiment, system 10 acts as an adaptive metronome that gradually gets the user back in sync, as opposed to resetting the pacing to the pace at time=0 s, as described above. For example, if the user/runner is going at 750 ms between footfalls but the goal is 1 second between footfalls, then system 10 takes the current pace and tries to gradually get the user to go to the target pace by going through gradual pacing, such as 850 ms, 900 ms and finally 1000 ms pacing. In this embodiment, a single haptic effect type can be used to regulate the pace.

As disclosed, a pacing system includes a feedback mechanism so that if the tracked pace is not consistent with the set pace, pacing cues or signals are used to restore the user to the set pace. The pacing cues and signals can be haptic effects, and different types of haptic effects can further be used to provide an indication on how the actual pace varies from the set pace. Embodiments can be used for any activity that will benefit from pacing. For example, for a cycling team, there might be multiple people receiving differing haptic cues depending on their pace. For dancing where dance partners or a dance team need to be synchronized there is a benefit for adjustable pacing. Sports such as swimming, rowing, speed walking, etc. that can benefit from a generally steady and adjustable cadence to pace strokes, steps, etc. can implement embodiments of the present invention. Other sports that utilize intervals of high intensity activity for a short period of time can benefit from the feedback based pacing. Further, the feedback can be a measurement of an attainment of a phase in any type of repetitive movement.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A method of pacing a user, the method comprising:
receiving a desired pace comprising a timing interval;
generating a first pace signal based on the desired pace and corresponding to the timing interval;
receiving feedback on an actual pace;
determining if the actual pace is different than the desired pace;
when the actual pace is different, generating a second pace signal having a timing that is different than the timing interval; and
when the actual pace is not different, generating the second pace signal in accordance with the timing interval;
wherein the timing interval comprises generating the first pace signal every t, wherein t is a first measure of time, further comprising:
determining that the actual pace differs from the desired pace by x, wherein x is a second measure of time;
generating a next pace signal at the next t interval after determining that the actual pace differs from the desired pace;
generating the second pace signal, after generating the next pace signal, at the next t+x interval when the actual pace is slower than the desired pace; and
generating the second pace signal, after generating the next pace signal, at the next t−x interval when the actual pace is faster than the desired pace.

2. The method of claim 1, wherein the first pace signal and the second pace signal each comprise one or more haptic effects that are vibratory.

3. The method of claim 1, wherein the first pace signal and the second pace signal each comprise one or more haptic effects generated by at least one of electrostatic friction, ultrasonic surface friction, an ultrasonic haptic transducer, a deformable surface or a shape changing device.

4. The method of claim 1, wherein the feedback is a measurement of a footfall.

5. The method of claim 1, wherein the feedback is a measurement of an attainment of a phase in a repetitive movement.

6. The method of claim 1, wherein the feedback is generated by an accelerometer.

7. The method of claim 1, wherein the determining if the actual pace is different than the desired pace comprises determining if a timing of a footfall is different from the timing interval within a predetermined range.

8. The method of claim 1, wherein the second pace signal comprises one of a plurality of types of haptic effects with a different haptic effect type to indicate whether the actual pace is slower or faster than the target pace, wherein the different haptic effect type comprises a variation of one or more haptic effect parameters.

9. The method of claim 8, wherein the haptic effect parameters comprise at least one of magnitude, frequency or duration.

10. The method of claim 1, further comprising receiving a sensor signal corresponding to the user's physical condition and wherein the timing of the second pace signal is based in part on the sensor signal.

11. The method of claim 1, wherein the first pace signal and the second pace signal each comprise one or more haptic effects generated by an actuator.

12. A non-transitory computer-readable medium having instructions stored thereon that, when executed by a processor, cause the processor to pace an activity, the pacing comprising:
receiving a desired pace comprising a timing interval;
generating a first pace signal based on the desired pace and corresponding to the timing interval;
receiving feedback on an actual pace;
determining if the actual pace is different than the desired pace;
when the actual pace is different, generating a second pace signal having a timing that is different than the timing interval; and
when the actual pace is not different, generating the second pace signal in accordance with the timing interval;
wherein the timing interval comprises generating the first pace signal every t, wherein t is a first measure of time, further comprising:
determining that the actual pace differs from the desired pace by x, wherein x is a second measure of time;
generating a next pace signal at the next t interval after determining that the actual pace differs from the desired pace;
generating the second pace signal, after generating the next pace signal, at the next t+x interval when the actual pace is slower than the desired pace; and
generating the second pace signal, after generating the next pace signal, at the next t−x interval when the actual pace is faster than the desired pace.

13. The computer-readable medium of claim 12, wherein the first pace signal and the second pace signal each comprise one or more haptic effects that are vibratory.

14. The computer-readable medium of claim 12, wherein the first pace signal and the second pace signal each comprise one or more haptic effects generated by at least one of electrostatic friction, ultrasonic surface friction, an ultrasonic haptic transducer, a deformable surface or a shape changing device.

15. The computer-readable medium of claim 12, wherein the feedback is a measurement of a footfall.

16. The computer-readable medium of claim 12, wherein the feedback is a measurement of an attainment of a phase in a repetitive movement.

17. The computer-readable medium of claim 12, wherein the feedback is generated by an accelerometer.

18. The computer-readable medium of claim 12, wherein the determining if the actual pace is different than the desired pace comprises determining if a timing of a footfall is different from the timing interval within a predetermined range.

19. The computer-readable medium of claim 12, wherein the second pace signal comprises one of a plurality of types of haptic effects with a different haptic effect type to indicate whether the actual pace is slower or faster than the target pace, wherein the different haptic effect type comprises a variation of one or more haptic effect parameters.

20. The computer-readable medium of claim 19, wherein the haptic effect parameters comprise at least one of magnitude, frequency or duration.

21. The computer-readable medium of claim 12, further comprising receiving a sensor signal corresponding to the user's physical condition and wherein the timing of the second pace signal is based in part on the sensor signal.

22. The computer-readable medium of claim 12, wherein the first pace signal and the second pace signal each comprise one or more haptic effects generated by an actuator.

23. A pacing system comprising:
a processor;
a pace signal output device coupled to the processor, wherein the pace signal output device comprises an actuator; and
a feedback device coupled to the processor;
wherein the processor is adapted to pace a user, the pacing comprising:
receiving a desired pace comprising a timing interval;
generating a first pace signal on the pace signal output device based on the desired pace and corresponding to the timing interval;
receiving feedback on an actual pace from the feedback device;
determining if the actual pace is different than the desired pace;
when the actual pace is different, generating a second pace signal on the pace signal output device having a timing that is different than the timing interval; and
when the actual pace is not different, generating the second pace signal on the pace signal output device in accordance with the timing interval;
wherein the timing interval comprises generating the first pace signal every t, wherein t is a first measure of time, further comprising:
determining that the actual pace differs from the desired pace by x, wherein x is a second measure of time;
generating a next pace signal at the next t interval after determining that the actual pace differs from the desired pace;
generating the second pace signal, after generating the next pace signal, at the next t+x interval when the actual pace is slower than the desired pace; and
generating the second pace signal, after generating the next pace signal, at the next t−x interval when the actual pace is faster than the desired pace.

24. The system of claim 23, wherein the pace signal output device comprises at least one of an electrostatic friction device, an ultrasonic surface friction device, an ultrasonic haptic transducer, a deformable surface or a shape changing device.

25. The system of claim 23, wherein the feedback device comprises an accelerometer.

26. The system of claim 23, wherein the second pace signal comprises one of a plurality of types of haptic effects with a different haptic effect type to indicate whether the actual pace is slower or faster than the target pace, wherein the different haptic effect type comprises a variation of one or more haptic effect parameters.

27. The system of claim 26, wherein the haptic effect parameters comprise at least one of magnitude, frequency or duration.

28. The system of claim 23, further comprising a sensor coupled to the processor, wherein the processor is further adapted to receive a sensor signal from the sensor corresponding to the user's physical condition, wherein the timing of the second pace signal is based in part on the sensor signal.

29. The system of claim 23, wherein the first pace signal and the second pace signal each comprise one or more haptic effects generated by an actuator.

* * * * *